United States Patent
Dyer

[19]

[11] Patent Number: 5,914,772
[45] Date of Patent: Jun. 22, 1999

[54] METHOD AND DEVICE FOR TESTING EYES

[75] Inventor: Alan McKenzie Dyer, Calgary, Canada

[73] Assignee: Eyelogic Inc., Canada

[21] Appl. No.: 08/987,851

[22] Filed: Dec. 9, 1997

[30] Foreign Application Priority Data

Aug. 29, 1997 [CA] Canada ................................. 2214260

[51] Int. Cl.$^6$ .......................................................... A61B 3/00
[52] U.S. Cl. ........................................... 351/246; 351/222
[58] Field of Search ................................... 351/246, 222, 351/223, 255, 200

[56] References Cited

U.S. PATENT DOCUMENTS

| | | |
|---|---|---|
| 3,880,501 | 4/1975 | Munnerlyn . |
| 4,697,895 | 10/1987 | Sekiguchi et al. . |
| 4,861,156 | 8/1989 | Terry . |
| 5,223,864 | 6/1993 | Twisselmann . |
| 5,329,322 | 7/1994 | Yancey . |
| 5,331,394 | 7/1994 | Shalon et al. . |
| 5,420,651 | 5/1995 | Kamppeter . |

FOREIGN PATENT DOCUMENTS

| | | |
|---|---|---|
| 2 129 963 | 5/1984 | United Kingdom . |
| WO 93/01744 | 2/1993 | WIPO . |

*Primary Examiner*—Hung Xuan Dang
*Attorney, Agent, or Firm*—Leonard Bloom

[57] ABSTRACT

The present invention relates to a device and methods for testing eyes. This method is objective in nature and can be performed by a technician, only requiring specialized personal to interpret the final prescription. The method comprises: Obtaining autorefractor, corrected autorefractor, and autolensometer results; Calculating sphere; Performing a Red-Green test; Calculating cylinder and axis; Determining minimum cylinder power; Determining final sphere; and Recording all data, wherein the steps of calculating sphere and calculating cylinder and axis do not rely upon subjective interpretation of responses made by the subject in order to complete the method. Furthermore, this method is capable of being fully processed by a computer so that a printout is produced that is suitable for interpretation by a refractionist.

16 Claims, 5 Drawing Sheets

NAME: TEST 1  AGE: 25  DATE: 05-23-1997

|  | RIGHT | | | | | | LEFT | | | | | |
|---|---|---|---|---|---|---|---|---|---|---|---|---|
|  | UNCORRECTED V.A. 400 (400) | | | | | | UNCORRECTED V.A. 400 (400) | | | | | |
|  | SPH | CYL | AX | ADD | VA | | SPH | CYL | AX | ADD | VA | |
| SUBJECTIVE | -6.25 | -0.50 | 11 |  | 20 | | -5.00 | -0.50 | 148 |  | 20 | |
|  | SPH | CYL | AX | ADD | PR | | SPH | CYL | AX | ADD | PR | |
| CORRECTED A.R. | -6.25 | -0.50 | 11 |  |  | | -4.75 | -0.75 | 156 |  |  | |
| AUTOREFRACTOR. | -5.75 | -0.50 | 6 |  |  | | -4.25 | -0.75 | 155 |  |  | |
| AUTOLENSOMETER. | -3.25 | -0.25 | 11 |  |  | | -2.75 | -1.00 | 156 |  |  | |

NAME: TEST 2  AGE: 57  DATE: 05-23-1997

|  | RIGHT | | | | | | LEFT | | | | | |
|---|---|---|---|---|---|---|---|---|---|---|---|---|
|  | UNCORRECTED V.A. 400 (400) | | | | | | UNCORRECTED V.A. 400 (400) | | | | | |
|  | SPH | CYL | AX | ADD | VA | | SPH | CYL | AX | ADD | VA |
| SUBJECTIVE | -6.75 | -1.00 | 21 | 2.50 | 20 | | -6.25 | -0.75 | 156 | 2.50 | 25 |
|  | SPH | CYL | AX | ADD | PR | | SPH | CYL | AX | ADD | PR |
| CORRECTED A.R. | -6.25 | -0.50 | 11 | | | | -4.75 | -0.75 | 156 | | |
| AUTOREFRACTOR. | -5.75 | -0.50 | 6 | | | | -4.25 | -0.75 | 155 | | |
| AUTOLENSOMETER. | -3.25 | -0.25 | 11 | | | | -2.75 | -1.00 | 156 | | |

FIGURE 2C

FIGURE 2D

METHOD AND DEVICE FOR TESTING EYES

BACKGROUND OF THE INVENTION

This invention pertains to devices and methods for testing eyes. More specifically this invention is directed to methods an automated system for determining refractive errors of the eye.

Testing refractive errors of the eye involves several tests, some of which are subjective, and other that are objective in nature. Objective refraction tests include the use of well known retinoscopy and autorefractors, while subjective refractions include a variety of tests that determine sphere, cylinder and axis. In these subjective tests targets are presented to a subject with a projector, or with illuminated wall charts. Lenses are changed manually using a manual phoropter, for example see U.S. Pat. No. 5,223,864 (Twisselmann, issued Jun. 29, 1993) or trial frames. With these manual methods, several procedures are subject to interpretation and error due to their subjective nature of implementation. Furthermore, a highly trained specialist is required to conduct these tests.

More recently efforts have been directed to the use of automated devices for the testing of refractive errors of the eye. Such devices include autorefractors, autolensometers, and autophoropters. For example U.S. Pat. No. 3,880,501 (Munnerlyn, issued Apr. 29, 1975) discloses a system for measuring refraction of eye that can be used manually or with automated refractors. U.S. Pat. No. 5,329,322 (Yancey, issued Jul. 12, 1994) discloses an autorefractor use to obtain refractions objectively and in a rapid manner using two images, and their reflected images, for differential comparison. A phoropter that can be manipulated by a control unit so that an operators movement can be minimized during the testing procedure (see for example U.S. Pat. No. 4,861,156, Terry issued Aug. 29, 1989) has also been disclosed. Shalon and Pund (U.S. Pat. No. 5,331,394, issued Jul. 19, 1994) disclose an autolensometer.

Several devices have been disclosed that further automate and reduce the subjective nature of eye testing. U.K. 2,129, 963 (Munnerlyn, published May 23, 1984) discloses an autorefractor that is interfaced with a computer and its method of use. The method involves providing a moving spot of light that varies in brightness, and recording the response of the patient's eye by video. E.P. 568,081 (Wutz et al, published Nov. 3, 1993) teaches of an eye testing device that uses a phoropter or refractometer interfaced with a computer that receives data and controls the function of the associated device. However, the process for testing eyes is essentially the same as that carried out in a regular eye test, and the process is simply computer controlled. The eye test procedure of Wutz et al. is still performed by a specialist, it exhibits minimal time saving benefits over conventional "hands-on" eye testing procedures, and involves several subjective testing procedures that are capable of introducing error into the final result. Preussner (WO 93/01744, published Jun. 27, 1992) discloses a computer controlled eye testing system to automate the eye testing procedure. The system incorporates the use of a computer that:

1) controls an autophoropter to place lenses in front of a subject,
2) directs test symbol displays,
3) queries the subject via an acoustic unit, and
4) determines the response by the subject via electronic keypad inputs.

This procedure, although more automated than that of Wutz et al in that it no longer requires a specialist for its operation, is still an automation of the conventional eye test procedure. Therefore, there is a need to develop methods and associated systems and devices that can be automated to reduce the subjective nature of the eye test procedure and that streamline the test procedure as well. Wutz et al or Preussner do not disclose new process steps to modify the eye test procedure, therefore, it is estimated that these procedures would take approximately 1 hour to complete. However, the procedure of this invention is complete within a 10 minute period of time. This time saving is due to the removal of the subjective testing and their replacement with novel tests that calculate refractive error.

With the method and system of this invention the operator makes no decisions regarding the progress or results of the test, thereby reducing the subjective nature of these tests. It is desirable that the outcome of these tests be in a form that is readily utilized by a specialist such as a refractionist for the preparation of suitable lenses for the subject. Furthermore, the procedure of this invention, by using a set of novel protocols involved in calculating sphere, cylinder and axis that are easily automated, results in the following desirable features:

1) removal of subjective analysis from eye test procedure;
2) produces a set of data easily interpreted by a refractionist;
3) produces more consistent lens prescriptions as denoted by fewer subjects requiring adjustments to their prescriptions;
4) permits the test procedure to be carried out by a technician without the need for a refractionist being present;
5) produces an output suitable for interpretation by a refractionist, optician, or ophthalmologist thereby permitting eye tests to take place in remote locations which otherwise do not have access to qualified specialists;
6) increases the time efficiency of the regular eye test procedure several fold.

SUMMARY OF INVENTION

This present invention relates to a system and method for the testing eyes. More specifically, this invention is directed to an automated system and associated methods for testing eyes.

According to the present invention there is provided a method for testing eyes comprising;

1) Obtaining autorefractor, corrected autorefractor, and autolensometer results;
2) Calculating sphere;
3) Performing a Red-Green test;
4) Calculating cylinder and axis;
5) Determining minimum cylinder power;
6) Determining final sphere; and
7) Recording all data.

This invention is also directed to a method comprising steps 1 to 7 as stated above, wherein the step of calculating the sphere (step 1) includes:

i) Obtain autorefractor and autolensometer results from file
ii) Apply regression equations for sphere cylinder and axis to these results in the autorefractor results.

This invention is also directed to a method comprising steps 1 to 7 as stated above, wherein the step of calculating the sphere (step 2) includes:

i) Calculating the spherical equivalent of regression corrected autorefractor result;
ii) Determining the expected unaided visual acuity using a visual acuity formula;
iii) Displaying a single letter of a size corresponding to that obtained in step ii) is presented to the subject;
iv) Determining if the response of a subject to the display of step iii) is correct or wrong;
   a) If the letter is correctly perceived then a repeat letter is displayed one size smaller and the display step (step iv) is repeated;
   b) If the subject incorrectly identifies the displayed letter, then a letter of one size larger is displayed;
   c) If this larger letter has not been previously tested then the display step (step iv) is repeated;
   d) If the letter has been previously displayed then proceed to next step (v).
v) Determining whether regression corrected autorefractor result (obtained from step i)) is myopic, and unaided acuity is better than largest letter available, if yes then proceed to step ix), other wise, proceed to step vi).
vi) Adding +2.00 diopter sphere to regression corrected autorefractor sphere.
vii) Sending the sphere, obtained from step vi), along with the regression corrected autorefractor cylinder and axis to the phoropter.
viii) Testing for visual acuity as in step iv) and storing the best visual acuity;
ix) Calculating spherical equivalent using the visual acuity formula (i.e. no cylinder and axis);
x) Converting the spherical equivalent to full correction (i.e. including sphere, cylinder and axis) using corrected autorefractor cylinder and axis result (obtained from step 1);
xi) Sending the full prescription to the autophoropter.

This invention also is directed to steps 1–7 of the above method wherein the step of determining cylinder and axis (step 3) comprises:
   i) A red-green test target consisting of two identical test type line of letters, one set on a red background the other on a green background is displayed using a display device.
   ii) Subject is queried as to whether:
      a) red is seen better than green;
      b) green seen better than red;
      c) both red and green appear equal;
      subjects responses are entered using a keyboard or other input device.
   iii) Lens change is sent to autophoropter of plus or minus 0.25 diopter according to response obtained in (step ii): if the result is:
      a) then add −0.25 diopters to spherical power currently present in the autophoropter and send this spherical lens change to the autophoropter; or
      b) then add +0.25 diopters to spherical power currently present in the autophoropter and send the spherical lens change to autophoropter; or
      c) then add −0.25 diopters to spherical power currently present in the autophoropter and send the spherical lens change to autophoropter; and
      repeat step i);
   iv) If response changes from red to green, then end test; otherwise,
   v) If response changes from green to red, add −0.25 diopter to spherical power currently present in autophoropter and send this spherical lens to autophoropter and end test;
   vi) If response changes from red to same to green, end test;
   vii) If response changes from green to same to red, then add −0.25 diopter to spherical power currently present in autophoropter, and send this spherical lens to autophoropter and end test;
   viii) If response changes from same to red, add −0.25 diopters to spherical power present at the start of the test and send this spherical lens change to autophoropter and repeat test from step i);
   ix) If response changes from same to green, add +0.25 diopters to spherical power present at the start of the test and send this spherical lens change to the autophoropter and repeat test from step i);
   x) If three consecutive responses of either red, green or same are obtained, then display a line of test types with a white background on the display device and send initial and final spherical lens to the autophoropter;
   xi) Determine subjects's preference for clarity between these two lenses as entered from the keyboard or other input device, retain preferred lens in autophoropter, and end test.

This invention also is directed to steps 1–7 of the above method wherein the step of determining cylinder and axis (step 4) comprises:
   i) Determining axis at which to set testing lens from axis of cylinder present in the phoropter;
   ii) Using a standard lens addition formula add testing cylinder power (+4 diopters) and axis obtained from i) to sphere cylinder and axis present in autophoropter;
   iii) Sending this lens combination to autophoropter;
   iv) Setting the angle of cylinder and axis test target to 90° to angle determined in step i) and displaying on a display device;
   v) Obtaining subjects responses using a keyboard or other device as to which line appears darker;
   vi) Determining whether the response is the more clockwise line, if so then rotate target 3 degrees clockwise, or if the response is the more counter clockwise line, then rotate the target 3 degrees counter clockwise;
   vii) Determining subjects response to a new position of the two lined astigmatic fan target;
      a) if response is the same as previous response then rotate target 3 degrees more in same direction;
      b) if nor the same, rotate target one degree in opposite direction;
   viii) Continuing with the above test to obtain first final angle until either;
      a) subject's response indicates no differences between darkness of lines;
      b) direction of rotating target is reversed a second time, in which case add or subtract 0.5 degree to last angle depending on last direction of rotation;
   ix) Recording the first final angle on file;
   x) Determining new axis for testing lens 45 degrees from first axis (derived from step i) and repeat steps i) to ix) to obtain second final angle, and record on file;
   xi) Determining subjects residual astigmatic correction using the first and second final angles obtained in steps ix) and x) and the testing lenses spheres cylinders and axes;
   xii) Obtaining the corrected residual astigmatic correction by applying the least cylinder power regression equation to the residual astigmatic correction derived from step xi);

xiii) Determining the calculated sphere, cylinder, and axis by adding the residual astigmatic correction (obtained from step xi)) to initial sphere cylinder and axis, using the lens addition formula;

xiv) Determining the regression-corrected-calculated sphere, cylinder, and axis by adding the corrected residual astigmatic correction (obtained from step xi) to the initial sphere, cylinder and axis (obtained in step 3, the red-green test result) using the lens addition formula and send this information is sent to the autophoropter;

xv) Displaying a line of test types on a display device;

xvi) Determining subjects preference for clarity of test types to both the initial sphere, cylinder and axis (obtained in step 3, the red-green test result), and to the regression-corrected-calculated sphere, cylinder, and axis (determined in step xiv));
  a) if the initial sphere, cylinder and axis is preferred, end procedure;
  b) if the regression-corrected-calculated sphere, cylinder, and axis is preferred then continue to step xvii);

xvii) Repeating step xvi) using the regression-corrected-calculated sphere, cylinder, and axis (determined in step xiv) and the calculated cylinder and axis (determined in step xiii) and store preferred lens combination in phoropter and end procedure.

This invention is also directed to the method using steps 1 to 7 wherein the step to find minimum cylinder power (step 5) comprises:

i) Displaying a line of test type on a display device;

ii) Determining minimum effective cylinder power by obtaining subject's preferences for clarity between 0.25 diopter changes in cylinder power; and iii) Selecting lower cylinder power when no preference is obtained when end point reached end test.

Furthermore, this invention pertains to the method of steps 1 to 7 wherein the step to find final sphere (step 6) comprises:

i) Obtaining subjects visual acuity from correct or wrong reading of test types;
  a) if correct, and type size read is larger than 20/20, reduce size of test type by one Snellen size;
  b) if wrong, increase test type by one Snellen type size and proceed to step ii);
  c) if correct and type size read is smaller than 20/20, proceed to step ii);

ii) Determining subject's preference between present (determined in step 4, xvi) or step xvii)) lens combination and a modified lens combination comprising the same lens combination with +0.25 sphere added when sent to phoropter;
  a) if present lens combination preferred, set present lens combination in phoropter and proceed to step iii);
  b) if the modified lens combination is preferred, or if there is no preferences, set lens combination with +0.25 diopter sphere added and repeat step i);

iii) Determining subject's preference between present (determined in step ii)) lens combination and a modified lens combination comprising the same lens combination with −0.25 sphere added when sent to phoropter;
  a) if present lens combination preferred or no preference, set present lens combination in phoropter and proceed to step iv);
  b) if modified lens combination is preferred, set present lens combination with −0.25 sphere added and repeat step iii);

iv) Determining visual acuity, if it is not 20/20 then reduce type size by one Snellen unit and proceed to step v), if visual acuity is 20/20 or better, end procedure;

v) Determining subject's response to reading test type as correct or wrong;
  a) if correct repeat step iv);
  b) if wrong increase visual acuity by one Snellen unit and end procedure.

This invention is also directed to a device for testing eyes comprising:
  an autorefractor,
  an autolensometer,
  an autophoropter,
  an input device,
  a display device,
  a printing device,
  at least one computer interfacing with each of these components,
wherein the computer is capable of querying and receiving data from the autorefractor, autolensometer, autophoropter, and a subject, and based on the responses obtained from the subject, the computer is capable of controlling the autophoropter;

wherein the querying and receiving data from the subject, and controlling the autorefractor, autolensometer, or autophoropter include:
  1) Obtaining autorefractor, corrected autorefractor, and autolensometer results;
  2) Calculating sphere;
  3) Performing a Red-Green test;
  4) Calculating cylinder and axis;
  5) Determining minimum cylinder power;
  6) Determining final sphere; and
  7) Record all data;
wherein steps 2 and 4 are as defined above.

BRIEF DESCRIPTION OF THE DRAWINGS

These and other features of the invention will become more apparent from the following description in which reference is made to the appended drawings wherein:

FIG. 2 shows examples of a standard test results obtained from: FIGS. 2A and 2B, a 25 year old subject and FIGS. 2C and 2D, a 57 year old subject using the method and system of this invention.

DESCRIPTION OF THE PREFERRED EMBODIMENT

Figure 1:
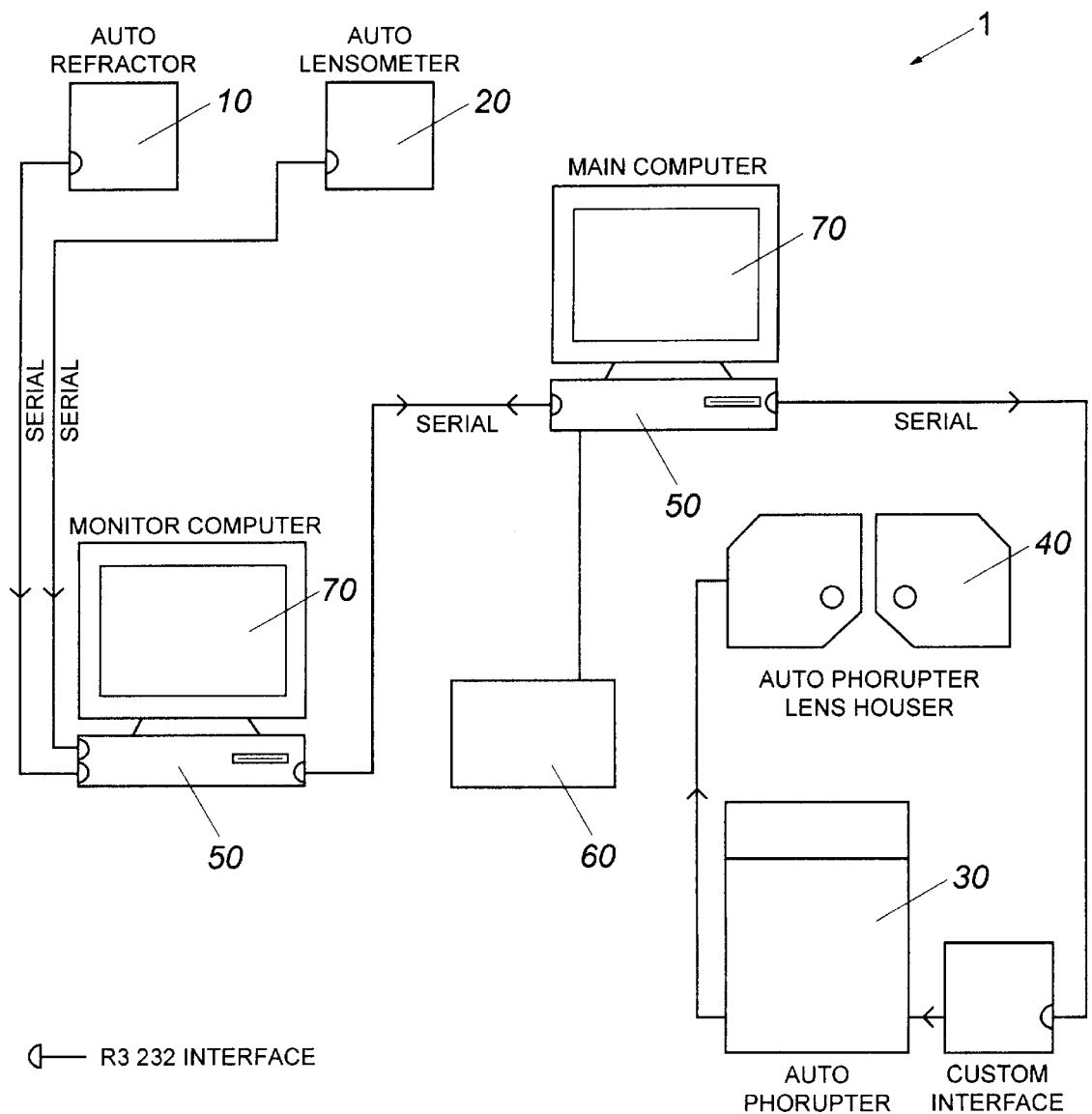
FIG. 1 shows the over all components of the eye testing system of an embodiment this invention.

The present invention is directed to the testing of refractive errors of the eye. More specifically, this invention incorporates subjective tests for the testing of eyes and presents a set of novel methods for the evaluation of refractive errors, including sphere, cylinder and axis.

Definitions

According to the present invention "sphere" (a spherical lens) is to mean a refracting medium bordered by two spherical coaxial surfaces of revolution. The surfaces can be convex or concave. The power of the lens is measured in diopters which is the reciprocal of the focal length of the lens.

By, "cylinder" (a cylindrical lens) it is meant a refracting medium bordered by two surfaces one of which forms par of a cylinder, the other of which is plane. Also, by "axis" it is meant the angle of the axis of the cylindrical refracting surface of a cylindrical lens relative to the horizontal. The power of the lens is also measured in diopters, By "visual acuity" it is meant the smallest angle subtended by an object to an eye which can be perceived by the eye. Furthermore, by "expected unaided visual acuity" it is meant the calculated visual acuity expected from an eye with any given refractive error without the aid of corrective lenses.

VISUAL ACUITY EQUATION

Calculated Sphere=a−b (log VA)

VA is visual acuity a and b are values determined by the regression equation.

By "regression corrected autorefractor sphere" it is meant the result obtained by applying a regression formula, derived from the regression analysis of previous autorefractor measurements of each entity with the corresponding subjective results of each entity, to the sphere, cylinder, and axis obtained in the autorefractor measurement for the eye currently being tested. Regression analysis is a standard statistical technique.

By "spherical equivalent" it is meant the single spherical lens which produces the same vergence of light as the average vergence of light of a combined spherical and cylindrical lens:

*Spherical equivalent=sphere power+½ cylinder power;*

*Sphere power=spherical equivalent+½ cylinder power.*

By "testing cylinder power" it is meant the dioptric value of the cylinder lens used to blur the image of the astigmatic target and is usually 4 diopters.

By "cylinder and axis testing target" it is meant a two lined astigmatic fan with the lines joined at one end and separated by an angle sufficient to give an adequate degree of blurring when viewed through a +diopter cylindrical lens. The lines are tapered to allow comparison through varying refractive errors. The thickness of the lines vary according to the last visual acuity of the subject (determined in step 2 xii) below) before the start of the calculated cylinder and axis test (see step 4, below).

By "residual astigmatic correction" it is meant the power and axis of the cylinder lens needed to correct the astigmatic refractive error present in the eye being tested. This is the end product of the cylinder and axis test.

By "a line of test types" it is meant the series of letters, all the same size, presented in a line on the display device.

By lens addition formula it is meant the standard formulas that would be known to one of skill in the art to calculate the resultant lens power and axis when two separate lenses are placed together coaxially. The following is an example of such a formula:

*S=(F1+F2−C)/2*

*C=square root((F1×F1)+(F2×F2)+(2 X F2×cos(2 X A)))*

Tan(2×B)=(F2×sin (2×A))/(F1+F2 cos(2×A))

Where, "F1" and "F2" are the dioptric power of first and second cylinder lenses, respectively, "A" is the angle between axis of first and second lens, "S" and "C" are the resultant spherical and cylindrical powers, respectively, and "B" is the angle of resultant cylinder axis in relation to axis of first cylinder lens.

With reference to FIG. 1, it can be seen that the eye test system (1) of this invention involves the use of an autorefractor (10), autolensometer (20), autophoropter (30) with lens holder (40) with associated input device that are manipulated by the operator or the subject in response to queries, and at least one computer (50) and associated printer (60) and display device (70). The computer interfaces with the autorefractor, autophoropter, autolensometer, display and input devices, and directs the different tests, analyses the data, and generates test types and testing targets that are presented to the subject on a display device. The interface allows the computer to set lenses in the autophoropter. More than one computer can be used to perform the refraction and generate testing targets, however, if less than two computers are used to oversee this process, then appropriate modifications to the computer may need to be carried out. For example, video cards may need to be introduced within the computer etc.

The testing procedure involves the following steps which are explained in more detail below:

1) Obtain autorefractor, corrected autorefractor, and autolensometer results
2) Calculate sphere
3) Perform Red-Green test
4) Calculating cylinder and axis
5) Determine minimum cylinder power
6) Determine final sphere
7) Change phoropter to test second eye and repeat steps 1–6
8) Record all data from both eyes.
1) Obtain autorefractor results.
   i) Obtain autorefractor and autolensometer results from file An autorefractor is an automated objective refracting instrument operated by a simple button push. This instrument is used to obtain an initial measurement of the subject eye being tested. No subject response is obtained. The autorefractor result has applied to it the regression equations for the three components of sphere, cylinder and axis to produce a corrected autorefractor result. The corrected autorefractor result is used as a starting point for the remainder of the test. Similarly, an autolensometer is used to objectively obtain the refractive power of eye glasses or contact lenses. Measurements are transmitted to a system computer and stored in a memory file.

The results obtained from the autorefractor are used to continually determine the accuracy of the refractions derived by the system of this invention. Regression equations for sphere cylinder and axis using final objective refraction results from the autorefractor, and results obtained from previous test results are calculated. These regression analysis are performed periodically following the analysis of a predetermined number of eyes. In one embodiment of this invention these results are obtained following the analysis of one hundred eyes, however, it is to be understood that other numbers of eye tests can be used prior to the determination. The regression which produces the highest correlation is used to produce a regression formula for each sphere, cylinder and axis. These formulas are then used to modify subsequent objective refractions, and calculate 95% confidence limits to asses accuracy of subsequent refractions. The corrected autorefractor result is a slightly more accurate measurement than the initial autorefractor result since consistent errors inherent in the instrument are eliminated by the regression analysis process.

ii) Apply regression equations for sphere cylinder and axis to these results in the autorefractor results 2) Calculate sphere.

There is no traditional equivalent of this. Traditionally, the spherical lens is tested subjectively by the duochrome test (red-green test) and by fogging techniques whereby +0.25 diopter lenses are sequentially placed in front of the subject's eye the image seen by the subject is perceptively blurred. Thereafter −0.25 diopter lenses are sequentially placed until the image attains maximum clarity. Both these techniques are incorporated in the system of this invention in automated form to verify the calculated sphere.

This calculation is performed by testing visual acuity without using corrective lenes, followed by lenses which fog vision. The testing type size presented to a subject decreases in size on a logarithmic scale instead of the conventional Snellen scale, which is an arbitrary scale with no mathematical relationship between the type sizes . The spherical equivalent of the refraction of the tested eye can then be calculated from a formula, known to one of skill in the art, using the visual acuities obtained from the fogging lenses used.

i) The spherical equivalent of regression corrected autorefractor result is calculated;

ii) The expected unaided visual acuity is determined using a visual acuity formula. This formula remains on file unaltered. This formula is derived by measuring unaided visual acuity of myopes between −0.25 and −4.00 diopters and by performing a regression analysis between unaided vision and degree of myopia;

iii) The calculated unaided acuity is sent to the computer and a single character of corresponding size is presented to the subject. This display may include the use of a monitor, or other system that would be known to one of skill in the art. The size of the character depends upon the size of the display device, the distance of the display device from the subject and the resolution of the display device. In the case of a computer monitor, the size of the screen affects the character size, and the size is measured in numbers of screen pixels (rather than conventional Snellen sizes);

iv) The subject is queried regarding the displayed character and the response is entered from a keyboard or other input device so that it can be determined if the response is correct or wrong. If the character is correctly perceived then a repeat character is displayed one size smaller and this display step (iv) is repeated. If the subject incorrectly identifies the displayed character, then a character of one size larger is displayed. If this larger character has not been previously tested then the display step (iv) is repeated. Otherwise if the character has been previously displayed then proceed to next step (v);

v) If regression corrected autorefractor result (obtained from step 1) is myopic, and unaided acuity is better than largest character available, then proceed to step ix), other wise, proceed to step vi);

vi) Add an increased diopter sphere, for example about +2.00 diopter sphere to regression corrected autorefractor sphere;

vii) The sphere, obtained from step vi), along with the regression corrected autorefractor cylinder and axis is sent to the autophoropter;

viii) Visual acuity is tested as in step iv) and the best visual acuity is filed stored;

xi) Calculate spherical equivalent (i.e. no cylinder and axis) using the visual acuity formula as above. The unaided acuity is used to calculate the spherical equivalent if the unaided acuity is obtained from step v), or, the best acuity is used for the calculation if the best acuity is obtained from step viii);

x) The spherical equivalent is converted to full correction (i.e. including sphere, cylinder and axis) using corrected autorefractor cylinder and axis (obtained from step 1(ii);

xi) The full prescription is sent to the autophoropter.

3) Perform Red-Green Test

This test is typically subjective in nature. It has therefore been altered from its regular form so that decision making by the operator is eliminated, however, the nature of the test remains unchanged.

i) A red-green test target consisting of two identical test type line of letters, one set on a red background the other on a green background is displayed using a display device.

ii) Subject is queried as to whether:
   a) red is seen better than green;
   b) green seen better than red;
   c) both red and green appear equal;

subjects responses are entered using a keyboard or other input device.

iii) Lens change is sent to autophoropter of plus or minus about 0.25 diopter according to response obtained in (step ii): if the result is:
   a) then add about −0.25 diopters to spherical power currently present in the autophoropter and send this spherical lens change to the autophoropter; or
   b) then add about +0.25 diopters to spherical power currently present in the autophoropter and send the spherical lens change to autophoropter; or
   c) then add about −0.25 diopters to spherical power currently present in the autophoropter and send the spherical lens change to autophoropter; and
repeat step i);

iv) If response changes from red to green, then end test; otherwise, v) If response changes from green to red, add about −0.25 diopter to spherical power currently present in autophoropter and send this spherical lens to autophoropter and end test;

vi) If response changes from red to same to green, end test;

vii) If response changes from green to same to red, then add about −0.25 diopter to spherical power currently present in autophoropter, and send this spherical lens to autophoropter and end test;

viii) If response changes from same to red, add about −0.25 diopters to spherical power present at the start of the test and send this spherical lens change to autophoropter and repeat test from step i);

ix) If response changes from same to green, add about +0.25 diopters to spherical power present at the start of the test and send this spherical lens change to the autophoropter and repeat test from step i);

x) If three consecutive responses of either red, green or same are obtained, then display a line of test types with a white background on the display device and send initial and final spherical lens to the autophoropter;

xi) Determine subjects's preference for clarity between these two lenses as entered from the keyboard or other input device, retain preferred lens in autophoropter, and end test.

4) Calculate cylinder and axis

Traditionally one or more of the following 3 tests are used.

1. Dial technique.

Target is a circle with radial lines forming spokes.

First meridian of the astigmatism is found by trial and error subjective testing with spherical lenses when subject perceives one of the lines in focus and others blurred.

Power of the cylinder lens is found by adding cylindrical lenses on axis of first meridian until all lines appear equally sharp.

2. Crossed Cylinder technique

A crossed cylinder is a lens which is the sum of two equally powered cylindrical lenses one concave (plus) and one convex (minus) whose axes are set at 90 degrees to each other.

Cylinder power is determined by "flipping" the lens so that the axes are reversed and determining with which setting the target is more clear. This is done in multiple trials until the clearest lens is obtained.

Cylinder axis is determined separately by placing the crossed cylinder lens axis at 45 degrees to the axis of the current cylindrical lens and flipping the lens. The axis of the current lens is altered 5 degrees in either direction according to the response and the process is repeated until the optimum axis is obtained.

3. Stenopaic slit.

This is an opaque lens with a meridional linear slit.

The lens is rotated in front of the eye until the clearest image is obtained. Spherical lenses are added to obtain maximum clarity. The lens is rotated 90 degrees and lenses again added to obtain maximum clarity.

However, none of these cylinders and axis techniques is incorporated in the system of this invention and all are replaced by the novel calculated cylinder and axis procedure described below.

In this invention the cylinder and axis of the astigmatism present in the subject eye are calculated simultaneously by placing a cylindrical lens of known power in front of the tested eye and presenting a two spoked astigmatic fan target to the subject. The target is rotated on the display device until there is no difference in clarity between the two spokes. This preformed twice with two different positions of the testing lens and target. The cylinder power and the axis of the lens required to correct the astigmatic error are calculated from the end angles of the target and the power of the testing lenses.

i) determining axis at which to set testing lens from axis of cylinder present in the autophoropter (for quicker lens changes, axis is close to that of cylinder present in autophoropter);

ii) Using a standard lens addition formula add testing cylinder power (about +4 diopters) and axis obtained from step i) to sphere cylinder and axis present in autophoropter (as determined at end of step 3);

iii) Send this lens combination to autophoropter;

iv) Setting the angle of cylinder and axis test target 90° to angle determined in step i) and displaying on the display device;

v) Obtain subjects responses using a keyboard or other device as to which line appears darker.

vi) Determining whether the response is the more clockwise line, if so then rotate target about 3 degrees clockwise, or if the response is the more counter clockwise line, then rotate the target about 3 degrees counter clockwise;

vii) Determine subjects response to new position target:
  a) if response is the same as previous response then rotate target about 3 degrees more in same direction;
  b) if nor the same, rotate target one degree in opposite direction.

viii) Continue test, to obtain first final angle, until either:
  a) subject's response indicates no differences between darkness of lines;
  b) direction of rotating target is reversed a second time, in which case add or subtract about 0.5 degree to last angle depending on last direction of rotation.

ix) Record first final angle on file.

x) Setting new axis for testing lens 45° from first axis (derived from step i) and repeat steps i) to ix) to obtain second final angle, and record on file;

xi) Determine subjects residual astigmatic correction using the first and second final angles obtained in steps ix) and x) and the testing lenses spheres cylinders and axes. Astigmatic corrections are calculated by modifying the lens addition formula to solve for the unknown values of the subjects residual cylinder and axis. This determination involves lens addition formulas to solve for the two unknowns. The known values for each equation are obtained from each of the two measurements (performed) obtained from steps ii, ix) and x)

xii) Obtain the corrected residual astigmatic correction by applying the minimum cylinder power regression equation to the residual astigmatic correction derived from step xi). The minimum cylinder power regression equation is derived from regression analysis between calculated cylinder powers and corresponding subjectively tested minimum cylinder powers for a number of subjects;

xiii) Determine the calculated sphere, cylinder, and axis by adding the residual astigmatic correction (obtained from step xi)) to initial sphere cylinder and axis, using the lens addition formula;

xiv) Determine the regression-corrected-calculated sphere, cylinder, and axis by adding the corrected residual astigmatic correction (obtained from step xi) to the initial sphere, cylinder and axis (obtained in step 3, end of red-green test) using the lens addition formula. This information is sent to the autophoropter;

xv) Display a line of test types on the display device such as a computer monitor;

xvi) Determine subjects preference for clarity of test types as entered from a keyboard or other input device to both the initial sphere, cylinder and axis (obtained in step 3, end of red-green test), and to the regression-corrected-calculated sphere, cylinder, and axis (determined in step xiv));
  a) if the initial sphere, cylinder and axis is preferred, end test;
  b) if the regression-corrected-calculated sphere, cylinder, and axis is preferred then continue to step xvii).

xvii) Repeat step xvi) using the regression-corrected-calculated sphere, cylinder, and axis (determined in step xiv) and the calculated cylinder and axis (determined in step xiii)). Store preferred lens combination in autophoropter and end test.

5) Find minimum cylinder power i) A line of test type is displayed on a monitor or other display device;

ii) Determining minimum effective cylinder power by obtaining subject's preferences for clarity between about 0.25 diopter changes in cylinder power; and iii) Selecting lower cylinder power when no preference is obtained when end point reached end test.

6) Find final sphere i) Display line of test type on display device and obtain subject's visual acuity from correct or wrong reading of test types as entered from a keyboard or other input device:
   a) if correct. and type size read is larger than 20/20, reduce size of test type by one Snellen size
   b) if wrong, increase test type by one Snellen type size and proceed to step ii)
   c) if correct and type size read is smaller than 20/20, proceed to step ii).

ii) Determine subject's preference, as entered through a keyboard or other input device, between present (determined in step 4, xvi) or xvii)) lens combination and a modified lens combination comprising the same lens combination with about +0.25 sphere added when sent to autophoropter;
   a) if present lens combination preferred, set present lens combination in autophoropter and proceed to step iii);
   b) if the modified lens combination is preferred, or if there is no preferences, set lens combination with about +0.25 diopter sphere added and repeat step i);

iii) Determine subject's preference, as entered through a keyboard or other input device, between present (determined in step ii)) lens combination and a modified lens combination comprising the same lens combination with about −0.25 sphere added when sent to (auto)phoropter.
   a) if present lens combination preferred or no preference, set present lens combination in autophoropter and proceed to step iv);
   b) if modified lens combination is preferred, set present lens combination with about −0.25 sphere added and repeat step iii);

iv) If visual acuity is not 20/20, as determined by step i), reduce type size by one Snellen unit and proceed to step v, if visual acuity is 20/20 or better, end test;

v) Determines subject's response to reading test type as correct or wrong, as entered through a keyboard or other input device;
   a) if correct repeat step iv);
   b) if wrong increase visual acuity by one Snellen unit and end test.

7) Test Second Eye

Change autophoropter, cover eye just tested and repeat step 1 to end of step 6.

8) Record all data from both eyes on file.

Figure 2B:
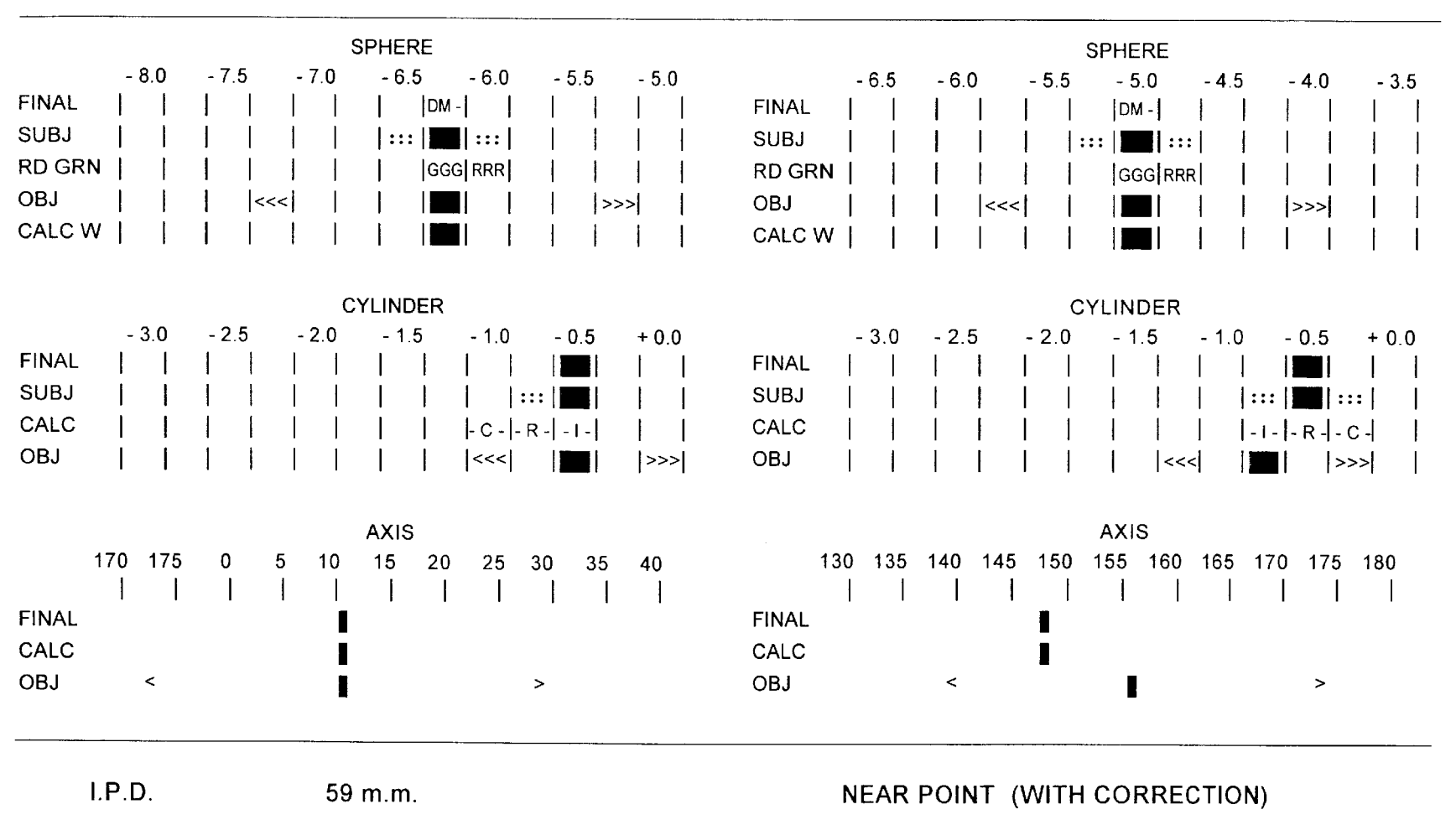
Figure 2D:
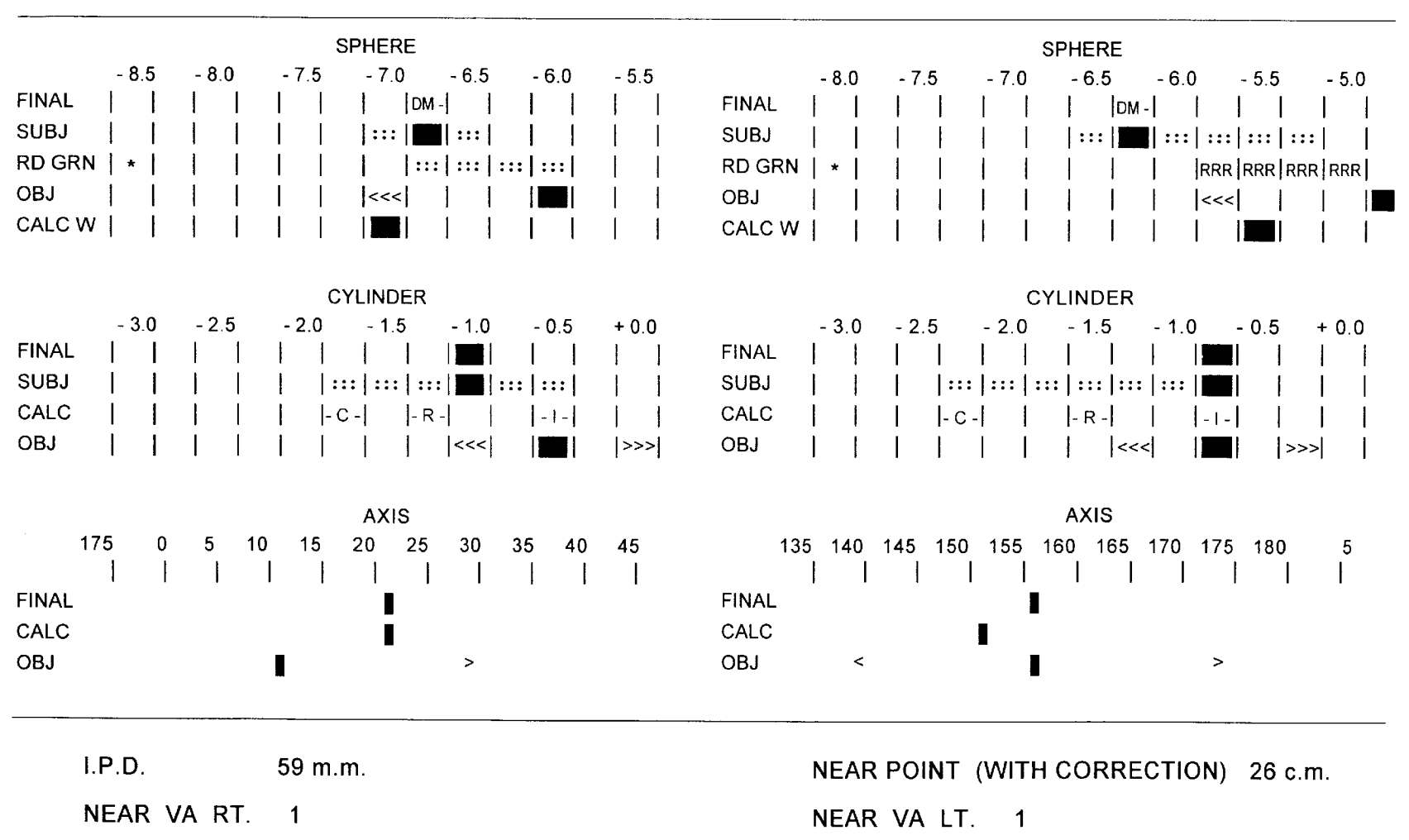

FIGS. 2 A, B, C and D show two standard results produced by the tests of this invention. The output includes:

Name, Age and Date.

Uncorrected Visual Acuity

First figure is a logarithmic Snellen number. Second figure in parenthesis is the closest conventional Snellen type size larger than the first figure.

Subjective

This is the final refraction result after completion of the test.

The VA result is the final visual acuity achieved with this refraction.

Corrected A.R.

This is the auto-refractor measurement after having been corrected with the regression equations currently on file. Regressing analysis is automatically performed after every 100 eyes are put on file. For the first 100 eyes refracted by the system no corrected A.R. will appear.

Autorefractor

This is the uncorrected autorefractor measurement.

Autolensometer

This is the autolensometer measurement of previous glasses.

Autokeratometer

This is the keratometer measurement if a combined AR/AK instrument is installed. This measurement has no effect on the refraction program.

Bar Charts

The three groups consist of the test results for sphere, cylinder and axis for each eye. For sphere and cylinder power each vertical column represents a lens power value. Powers range over three diopters in quarter diopter increments around the subject's refraction values. For axis values each column represents a value in a range of 50 degrees in 5 degree increments.

Sphere

Final

M is the final sphere result after completion of the test.

D is the final sphere result corrected to allow for the testing distance of the system.

Subjective

Solid bars indicate the lens preferred by the subject during the subjective portion of the test. More than one solid bar indicates that the subject could distinguish no difference between the lenses shown.

Dotted bars indicate the other lenses tested and not preferred by the subject.

Red Green

Duochrome test results.

GGG represents the lens power with which the letters on the green background were seen more clearly.

RRR represents the lens power with which the letters on the red background were seen more clearly.

Dotted bars represent the lens power with which both groups of letters were seen equally clearly.

Objective

The solid bar represents the regression corrected autorefractor sphere power value. This value is also corrected according to changes in the cylinder power which may have occurred during the cylinder test.

The right and left arrows mark the upper and lower values of the 95% confidence limits of the correlation between objective and subjective refractions.

Calc W

This is the power of the spherical correction calculated by the program in the auto test only (F8).

A value to the left (more minus) of the other tests on the sphere chart indicates that instrument accommodation on the autorefractor is less likely to have occurred.

A value to the right (more plus) of the other tests on the sphere chart indicates that instrument accommodation occurred during the autorefractor measurement or that the subject produced a pinhole effect by squinting during the initial acuity test.

Cylinder

Final

The solid bar is the final cylinder power value at the completion of the test.

Subjective

Solid bars indicate the most plus cylinder lens power with which the subject could not subjectively appreciate a fogging of the test types.

Dotted bars represent the powers of the lenses tested.

Calc.

I is the cylinder lens power set before the start of the test.

C is the calculated cylinder lens power.

R is the regression corrected value of the cylinder lens power.

Objective

The solid bar represents the regression corrected autorefractor cylinder power value.

The right and left arrows mark the upper and lower values of the 95% confidence limits of the correlation between objective and subjective refractions.

Axis

Final

The solid bar is the final cylinder axis value at the completion of the test.

Calc.

The solid bar is the calculated cylinder axis value.

Objective

The solid bar represents the regression corrected autorefractor cylinder axis value.

The right and left arrows mark the upper and lower values of the 95% confidence limits of the correlation between objective and subjective refractions.

IPD

Pupillary distance measured on the autorefractor.

Near Point

Measured during reading of small text test and measured with reading correction set.

Near Visual Acuity

Entered from keyboard during near test.

Tonometry

If done, results are entered from keyboard at conclusion of test.

Steps for interpreting printouts

1. Corrected visual acuity should be no worse than 20/25.
2. Bar Charts. (see FIGS. 2B, and D)

Sphere

Black bars ideally should be vertically aligned in objective, subjective and calculated results.

Red green line ideally should have no dotted bars and one each RRR and GGG bars and either should be aligned vertically with the black bars of the other sphere results.

Cylinder

The C value should be vertically aligned with the objective black bar. If an over-refraction has been performed, the I, C and R should be close together.

Axis

Objective and calculated axes should not be widely separated if cylinder power more minus than −0.50 D.

INDICATORS OF LESS SATISFACTORY TESTS i. More than one black bar on any one subjective line.
ii. Red green either all RRR, all GGG or all dotted bars.
iii. Lack of vertical alignment of results.
iv. Subjective results outside 95% confidence limits of objective results.
v. Evidence of over accommodation during test
 a) Calculated sphere more plus than other results.
 b) Sphere bar chart results sloping from upper left corner to lower right corner.
 c) Age under 40.
vi. Evidence of irregular astigmatism
 a) I, R and C widely separated when over-refraction performed.
 b) Wide separation of calculated and objective cylinder and axis results.
3. Reading of small text should be appropriate for age.
4. Change from previous prescriptions should be consistent with age and refractive error.

The present invention has been described with regard to preferred embodiments. However, it will be obvious to persons skilled in the art that a number of variations and modifications can be made without departing from the scope of the invention as described in the following claims.

What is claimed is:

1. A method for the testing of an eye of a subject comprising;
 1) Obtaining autorefractor, corrected autorefractor, and autolensometer results;
  i) Obtain initial autorefractor and autolensometer and store results to a file;
  ii) Apply regression equations for sphere cylinder and axis to the autorefractor results of step i) to obtain regression corrected autorefractor results and record data to the file;
 2) Calculating sphere,
  i) Calculating the spherical equivalent of regression corrected autorefractor;
  ii) Determining the expected unaided visual acuity using a visual acuity formula;
  iii) Displaying a character of a size corresponding to that obtained in step ii)2 is presented to the subject;
  iv) Determining if the response of a subject is correct or wrong;
  v) Determining whether regression corrected autorefractor result (obtained from step i) is myopic, and unaided acuity is better than largest character available, if yes then proceed to step ix), other wise, proceed to step vi);
  vi) Adding an increased diopter sphere to regression corrected autorefractor sphere;
  vii) Sending the sphere, obtained from step vi), along with the regression corrected autorefractor cylinder and axis to the phoropter;
  viii) Testing for visual acuity as in step iv) and storing the best visual acuity;
  ix) Calculating spherical equivalent using the visual acuity formula;
  x) Converting the spherical equivalent to full correction using corrected autorefractor cylinder and axis results (obtained from step 1):
  xi) Sending the full prescription to the autophoropter and recording data to the file;
 3) Performing a Red-Green test and storing results to the file;
 4) Calculating cylinder and axis and store preferred lens combination in phoropter and to the file;
 5) Determining minimum cylinder power and storing data to the file;
 6) Determining final sphere and storing data to the file;
 7) Recording all data obtained from steps 1 to 6,
wherein the steps of calculating sphere (step 2), and calculating cylinder and axis (step 4) do not rely upon subjective interpretation of responses made by the subject.

2. The method of claim 1 wherein the method is used to test two eyes and steps 1 to 7 are preformed on the first eye, followed by the testing of the second eye.

3. The method of claim 2, wherein the step of calculating the sphere (step 2 part iv)) includes:

iv) Determining if the response of a subject to the display of step iii) is correct or wrong;
    a) If the character is correctly perceived then a repeat character is displayed one size smaller and the display step (step iv) is repeated;
    b) If the subject incorrectly identifies the displayed character, then a character of one size larger is displayed;
    c) If this larger character has not been previously tested then the display step (step iv) is repeated;
    d) If the character has been previously displayed then proceed to next step (v).

4. The method of claim 2 wherein the step of determining cylinder and axis (step 4) comprises:

i) Determining axis at which to set testing lens from axis of cylinder present in the phoropter;
  ii) Using a standard lens addition formula add testing cylinder power (+4 diopters) and axis obtained from step i) to sphere cylinder and axis present in autophoropter (as determined at end of step 3);
  iii) Sending this lens combination to autophoropter;
  iv) Setting the angle of cylinder and axis test target 90° to angle determined in step i) and displaying on a display device;
  v) Obtaining subjects responses using a keyboard or other device as to which line appears darker;
  vi) Determining whether the response is the more clockwise line, if so then rotate target about 3 degrees clockwise, or if the response is the more counter clockwise line, then rotate the target about 3 degrees counter clockwise;
  vii) Determining subjects response to a new position of the two lined astigmatic fan target;
    a) if response is the same as previous response then rotate target about 3 degrees more in same direction;
    b) if nor the same, rotate target one degree in opposite direction;
  viii) Continuing with the above test to obtain first final angle until either;
    a) subject's response indicates no differences between darkness of lines;
    b) direction of rotating target is reversed a second time, in which case add or subtract about 0.5 degree to last angle depending on last direction of rotation;
  ix) Recording the first final angle on file;
  x) Setting new axis for testing lens 45° from first axis (derived from step i) and repeat steps i) to ix) to obtain second final angle, and record on file;
  xi) Determining subjects residual astigmatic correction using the first and second final angles obtained in steps ix) and x) and the testing lenses spheres cylinders and axes;
  xii) Obtaining the corrected residual astigmatic correction by applying the least cylinder power regression equation to the residual astigmatic correction derived from step xi);
  xiii) Determining the calculated sphere, cylinder, and axis by adding the residual astigmatic correction (obtained from step xi)) to initial sphere cylinder and axis, using the lens addition formula;
  xiv) Determining the regression-corrected-calculated sphere, cylinder, and axis by adding the corrected residual astigmatic correction (obtained from step xi) to the initial sphere, cylinder and axis (obtained in step 3, the red-green test) using the lens addition formula and send this information is sent to the autophoropter;
  xv) Displaying a line of test types on a display device;
  xvi) Determining subjects preference for clarity of test types to both the initial sphere, cylinder and axis (obtained in step 3, the red-green test), and to the regression-corrected-calculated sphere, cylinder, and axis (determined in step xiv));
    a) if the initial sphere, cylinder and axis is preferred, end procedure;
    b) if the regression-corrected-calculated sphere, cylinder, and axis is preferred then continue to step xvii);
  xvii) Repeating step xvi) using the regression-corrected-calculated sphere, cylinder, and axis (determined in step xiv) and the calculated cylinder and axis (determined in step xiii) and store preferred lens combination in phoropter and end procedure.

5. The method of claim 2 wherein the step to find minimum cylinder power (step 5) comprises:

i) Displaying a line of test type on a display device;
  ii) Determining minimum effective cylinder power by obtaining subject's preferences for clarity between about 0.25 diopter changes in cylinder power; and
  iii) Selecting lower cylinder power when no preference is obtained when end point reached end test.

6. The method of claim 2 wherein the step to find final sphere (step 6) comprises:

i) Obtaining subjects visual acuity from correct or wrong reading of test types;
    a) if correct; and type size read is larger than 20/20, reduce size of test type by one Snellen size;
    b) if wrong, increase test type by one Snellen type size and proceed to step ii);
    c) if correct and type size read is smaller than 20/20, proceed to step ii);
  ii) Determining subject's preference between present (determined in step 4, xvi or step xvii)) lens combination and a modified lens combination comprising the same lens combination with about +0.25 sphere added when sent to phoropter;
    a) if present lens combination preferred, set present lens combination in phoropter and proceed to step iii);
    b) if the modified lens combination is preferred, or if there is no preferences, set lens combination with about +0.25 diopter sphere added and repeat step i);
  iii) Determining subject's preference between present (determined in step ii)) lens combination and a modified lens combination comprising the same lens combination with about −0.25 sphere added when sent to phoropter;
    a) if present lens combination preferred or no preference, set present lens combination in phoropter and proceed to step iv);
    b) if modified lens combination is preferred, set present lens combination with about −0.25 sphere added and repeat step iii);
  iv) Determining visual acuity, if it is not 20/20 then reduce type size by one Snellen unit and proceed to step v), if visual acuity is 20/20 or better, end procedure;
  v) Determining subject's response to reading test type as correct or wrong;

a) if correct repeat step iv);
b) if wrong increase visual acuity by one Snellen unit and end procedure.

7. The method of claim 2 wherein steps 1 to 7 comprise:
iv) Determining if the response of a subject to the display of step iii) is correct or wrong;
   a) If the character is correctly perceived then a repeat character is displayed one size smaller and the display step (step iv)is repeated;
   b) If the subject incorrectly identifies the displayed character, then a character of one size larger is displayed;
   c) If this larger character has not been previously tested then the display step (step iv) is repeated;
   d) If the character has been previously displayed then proceed to next step (v);
3) Performing Red-Green Test,
   i) Displaying a red-green test target consisting of two identical test type line of letters, one set on a red background the other on a green background on a display device;
   ii) Determining whether the subject sees:
      a) red is seen better than green;
      b) green seen better than red;
      c) both red and green appear equal;
   subjects responses are entered using a keyboard or other input device;
   iii) Lens change is sent to autophoropter of plus or minus 0.25 diopter according to response obtained in (step ii): if the result is:
      a) then add about −0.25 diopters to spherical power currently present in the autophoropter and send this spherical lens change to the autophoropter; or
      b) then add about +0.25 diopters to spherical power currently present in the autophoropter and send the spherical lens change to autophoropter; or
      c) then add about −0.25 diopters to spherical power currently present in the autophoropter and send the spherical lens change to autophoropter; and repeat step i);
   iv) If response changes from red to green, then end test; otherwise,
   v) If response changes from green to red, add about −0.25 diopter to spherical power currently present in autophoropter and send this spherical lens to autophoropter and end test;
   vi) If response changes from red to same to green, end test;
   vii) If response changes from green to same to red, then add about −0.25 diopter to spherical power currently present in autophoropter, and send this spherical lens to autophoropter and end test;
   viii) If response changes from same to red, add about −0.25 diopters to spherical power present at the start of the test and send this spherical lens change to autophoropter and repeat test from step i);
   ix) If response changes from same to green, add about +0.25 diopter to spherical power present at the start of the test and send this spherical lens change to the autophoropter and repeat test from step i);
   x) If three consecutive responses of either red, green or same are obtained, then display a line of test types with a white background on the display device and send initial and final spherical lens to the autophoropter;
   xi) Determine subjects's preference for clarity between these two lenses as entered from the keyboard or other input device, retain preferred lens in autophoropter, and end test;
4) Calculating cylinder and axis,
   i) Determining axis at which to set testing lens from axis of cylinder present in the phoropter;
   ii) Using a standard lens addition formula add testing cylinder power (+4 diopters) and axis obtained from step i) to sphere cylinder and axis present in autophoropter (as determined at end of step 3);
   iii) Sending this lens combination to autophoropter;
   iv) Setting the angle of cylinder and axis test target 90° to angle determined in step i) and displaying on the display device;
   v) Obtaining subjects responses using a keyboard or other device as to which line appears darker;
   vi) Determining whether the response is the more clockwise line, if so then rotate target about 3 degrees clockwise, or if the response is the more counter clockwise line, then rotate the target about 3 degrees counter clockwise;
   vii) Determining subjects response to a new position of the two lined astigmatic fan target;
      a) if response is the same as previous response then rotate target about 3 degrees more in same direction;
      b) if nor the same, rotate target one degree in opposite direction;
   viii) Continuing with the above test to obtain first final angle until either;
      a) subject's response indicates no differences between darkness of lines;
      b) direction of rotating target is reversed a second time, in which case add or subtract 0.5 degree to last angle depending on last direction of rotation;
   ix) Recording the first final angle on file;
   x) Setting new axis for testing lens 45° from first axis (derived from step i) and repeat steps i) to ix) to obtain second final angle, and record on file;
   xi) Determining subjects residual astigmatic correction using the first and second final angles obtained in steps ix) and x) and the testing lenses spheres cylinders and axes;
   xii) Obtaining the corrected residual astigmatic correction by applying the least cylinder power regression equation to the residual astigmatic correction derived from step xi);
   xiii) Determining the calculated sphere, cylinder, and axis by adding the residual astigmatic correction (obtained from step xi)) to initial sphere cylinder and axis, using the lens addition formula;
   xiv) Determining the regression-corrected-calculated sphere, cylinder, and axis by adding the corrected residual astigmatic correction (obtained from step xi) to the initial sphere, cylinder and axis (obtained in step 3, the red-green test) using the lens addition formula and send this information is sent to the autophoropter;
   xv) Displaying a line of test types on a display device;
   xvi) Determining subjects preference for clarity of test types to both the initial sphere, cylinder and axis (obtained in step 3, the red-green test), and to the regression-corrected-calculated sphere, cylinder, and axis (determined in step xiv));
      a) if the initial sphere, cylinder and axis is preferred, end procedure;
      b) if the regression-corrected-calculated sphere, cylinder, and axis is preferred then continue to step xvii);

xvii) Repeating step xvi) using the regression-corrected-calculated sphere, cylinder, and axis (determined in step xiv) and the calculated cylinder and axis (determined in step xiii) and store preferred lens combination in phoropter and end procedure;

5) Determining minimum cylinder power
   i) Displaying a line of test type on a display device;
   ii) Determining minimum effective cylinder power by obtaining subject's preferences for clarity between about 0.25 diopter changes in cylinder power; and
   iii) Selecting lower cylinder power when no preference is obtained when end point reached end test;

6) Finding final sphere
   i) Displaying a line of test type on display device and obtaining subjects visual acuity from correct or wrong reading of test types;
      a) if correct. and type size read is larger than 20/20, reduce size of test type by one Snellen size;
      b) if wrong, increase test type by one Snellen type size and proceed to step ii);
      c) if correct and type size read is smaller than 20/20, proceed to step ii);
   ii) Determining subject's preference between present (determined in step 4, xvi or step xvii)) lens combination and a modified lens combination comprising the same lens combination with about +0.25 sphere added when sent to phoropter;
      a) if present lens combination preferred, set present lens combination in phoropter and proceed to step iii);
      b) if the modified lens combination is preferred, or if there is no preferences, set lens combination with about +0.25 diopter sphere added and repeat step i);
   iii) Determining subject's preference between present (determined in step ii)) lens combination and a modified lens combination comprising the same lens combination with about −0.25 sphere added when sent to autophoropter;
      a) if present lens combination preferred or no preference, set present lens combination in autophoropter and proceed to step iv);
      b) if modified lens combination is preferred, set present lens combination with about −0.25 sphere added and repeat step iii);
   iv) Determining visual acuity, if it is not 20/20 then reduce type size by one Snellen unit and proceed to step v), if visual acuity is 20/20 or better, end procedure;
   v) Determining subject's response to reading test type as correct or wrong;
      a) if correct repeat step iv);
      b) if wrong increase visual acuity by one Snellen unit and end procedure;

7) Changing autophoropter, cover eye just tested and repeat step 1 to end of step 6 on second eye;
8) Recording all data from both eyes on file.

8. The method of claim 7 wherein the responses obtained from the subject are processed by a computer in order to produce an output.

9. The method of claim 8, wherein the results obtained from the autophoropter, autorefractor, and autolensometer are included on the output.

10. The method of claim 1 wherein the responses obtained from the subject are processed by a computer in order to produce an output.

11. The method of claim 10, wherein the results obtained from the autophoropter, autorefractor, and autolensometer are included on the output.

12. A device for testing eyes comprising:
an autorefractor,
an autolensometer,
an autophoropter
a display device,
an input device,
a printing device, and,
at least one computer interfacing with each of these components,
wherein the computer is capable of querying and receiving data from a subject and based on the responses obtained from the subject, as entered through the input device, controlling the autorefractor, autolensometer, or autophoropter, and displaying test patterns on the display device as well as printing as needed;
wherein the querying and receiving data from the subject, and controlling the autorefractor, autolensometer, or autophoropter include:
   1) Obtaining autorefractor, corrected autorefractor, and autolensometer results;
   2) Calculating sphere;
   3) Performing a Red-Green test;
   4) Determining cylinder and axis;
   5) Determining minimum cylinder power;
   6) Determining final sphere;
   7) Record all data; and
wherein the step of calculating sphere (step 2) comprises:
   i) Calculating the spherical equivalent of regression corrected autorefractor result;
   ii) Determining the expected unaided visual acuity using a visual acuity formula;
   iii) Displaying a single letter of a size corresponding to that obtained in step ii) is presented to the subject;
   iv) Determining if the response of a subject to the display of step iii) is correct or wrong;
      a) If the character is correctly perceived then a repeat character is displayed one size smaller and the display step (step iv) is repeated;
      b) If the subject incorrectly identifies the displayed character, then a character of one size larger is displayed;
      c) If this larger character has not been previously tested then the display step (step iv) is repeated;
      d) If the character has been previously displayed then proceed to next step (v);
   v) Determining whether regression corrected autorefractor result (obtained from step i) is myopic, and unaided acuity is better than largest letter available, if yes then proceed to step ix), other wise, proceed to step vi);
   vi) Adding an increased diopter sphere to regression corrected autorefractor sphere;
   vii) Sending the sphere, obtained from step vi), along with the regression corrected autorefractor cylinder and axis to the phoropter;
   viii) Testing for visual acuity as in step iv) and storing the best visual acuity;
   ix) Calculating spherical equivalent using the visual acuity formula;
   x) Converting the spherical equivalent to full correction using corrected autorefractor cylinder and axis (obtained from step 1);

xi) Sending the full prescription to the autophoropter.

13. The device of claim 12, wherein the step of determining cylinder and axis (step 4) comprises:
 i) Determining axis at which to set testing lens from axis of cylinder present in the phoropter;
 ii) Using a standard lens addition formula add testing cylinder power (about +4 diopters) and axis obtained from step i) to sphere cylinder and axis present in autophoropter (as determined at end of step 3);
 iii) Sending this lens combination to autophoropter;
 iv) Setting the angle of cylinder and axis test target 90° to angle determined in step i) and displaying on the display device;
 v) Obtaining subjects responses using a keyboard or other device as to which line appears darker;
 vi) Determining whether the response is the more clockwise line, if so then rotate target about 3 degrees clockwise, or if the response is the more counter clockwise line, then rotate the target about 3 degrees counter clockwise;
 vii) Determining subjects response to a new position of the two lined astigmatic fan target;
  a) if response is the same as previous response then rotate target about 3 degrees more in same direction;
  b) if nor the same, rotate target one degree in opposite direction;
 viii) Continuing with the above test to obtain first final angle until either;
  a) subject's response indicates no differences between darkness of lines;
  b) direction of rotating target is reversed a second time, in which case add or subtract about 0.5 degree to last angle depending on last direction of rotation;
 ix) Recording the first final angle on file;
 x) Setting new axis for testing lens 45° from first axis (derived from step i) and repeat steps i) to ix) to obtain second final angle, and record on file;
 xi) Determining subjects residual astigmatic correction using the first and second final angles obtained in steps ix) and x) and the testing lenses spheres cylinders and axes;
 xii) Obtaining the corrected residual astigmatic correction by applying the least cylinder power regression equation to the residual astigmatic correction derived from step xi);
 xiii) Determining the calculated sphere, cylinder, and axis by adding the residual astigmatic correction (obtained from step xi)) to initial sphere cylinder and axis, using the lens addition formula;
 xiv) Determining the regression-corrected-calculated sphere, cylinder, and axis by adding the corrected residual astigmatic correction (obtained from step xi) to the initial sphere, cylinder and axis (obtained in step 3, the red-green test) using the lens addition formula and send this information is sent to the autophoropter;
 xv) Displaying a line of test types on a display device;
 xvi) Determining subjects preference for clarity of test types to both the initial sphere, cylinder and axis (obtained in step 3, the red-green test), and to the regression-corrected-calculated sphere, cylinder, and axis (determined in step xiv));
  a) if the initial sphere, cylinder and axis is preferred, end procedure;
  b) if the regression-corrected-calculated sphere, cylinder, and axis is preferred then continue to step xvii);
 xvii) Repeating step xvi) using the regression-corrected-calculated sphere, cylinder, and axis (determined in step xiv) and the calculated cylinder and axis (determined in step xiii) and store preferred lens combination in phoropter and end procedure.

14. The device of claim 12 wherein steps 1 to 7 comprise:
 1) Obtaining autorefractor results,
  i) Obtain autorefractor and autolensometer results from file;
  ii) Apply regression equations for sphere cylinder and axis to these results in the autorefractor results to obtain corrected autorefractor results;
 2) Calculating sphere,
  i) Calculating the spherical equivalent of regression corrected autorefractor;
  ii) Determining the expected unaided visual acuity using a visual acuity formula;
  iii) Displaying a single letter of a size corresponding to that obtained in step ii) is presented to the subject;
  iv) Determining if the response of a subject to the display of step iii) is correct or wrong;
   a) If the character is correctly perceived then a repeat character is displayed one size smaller and the display step (step iv)is repeated;
   b) If the subject incorrectly identifies the displayed character, then a character of one size larger is displayed;
   c) If this larger character has not been previously tested then the display step (step iv) is repeated;
   d) If the character has been previously displayed then proceed to next step (v);
  v) Determining whether regression corrected autorefractor result (obtained from step i) is myopic, and unaided acuity is better than largest letter available, if yes then proceed to step ix), other wise, proceed to step vi);
  vi) Adding an increased diopter sphere to regression corrected autorefractor sphere;
  vii) Sending the sphere, obtained from step vi), along with the regression corrected autorefractor cylinder and axis to the phoropter;
  viii) Testing for visual acuity as in step iv) and storing the best visual acuity;
  ix) Calculating spherical equivalent using the visual acuity formula;
  x) Converting the spherical equivalent to full correction using corrected autorefractor cylinder and axis (obtained from step 1);
  xi) Sending the full prescription to the autophoropter;
 3) Performing Red-Green Test,
  i) Displaying a red-green test target consisting of two identical test type line of letters, one set on a red background the other on a green background on a display device;
  ii) Determining whether the subject sees:
   a) red is seen better than green;
   b) green seen better than red;
   c) both red and green appear equal;
 subjects responses are entered using a keyboard or other input device;
  iii) Lens change is sent to autophoropter of plus or minus about 0.25 diopter according to response obtained in (step ii): if the result is:
   a) then add about −0.25 diopters to spherical power currently present in the autophoropter and send this spherical lens change to the autophoropter; or
   b) then add about +0.25 diopters to spherical power currently present in the autophoropter and send the spherical lens change to autophoropter; or c) then add about −0.25 diopters to spherical power currently present in the autophoropter and send the spherical lens change to autophoropter; and repeat step i);

iv) If response changes from red to green, then end test; otherwise, v) If response changes from green to red, add about −0.25 diopter to spherical power currently present in autophoropter and send this spherical lens to autophoropter and end test;

vi) If response changes from red to same to green, end test;

vii) If response changes from green to same to red, then add about −0.25 diopter to spherical power currently present in autophoropter, and send this spherical lens to autophoropter and end test;

viii) If response changes from same to red, add about −0.25 diopters to spherical power present at the start of the test and send this spherical lens change to autophoropter and repeat test from step i);

ix) If response changes from same to green, add about +0.25 diopters to spherical power present at the start of the test and send this spherical lens change to the autophoropter and repeat test from step i);

x) If three consecutive responses of either red, green or same are obtained, then display a line of test types with a white background on the display device and send initial and final spherical lens to the autophoropter;

xi) Determine subjects's preference for clarity between these two lenses as entered from the keyboard or other input device, retain preferred lens in autophoropter, and end test;

4) Calculating cylinder and axis, i) Determining axis at which to set testing lens from axis of cylinder present in the phoropter;

ii) Using a standard lens addition formula add testing cylinder power (a +4 diopters) and axis obtained from step i) to sphere cylinder and axis present in autophoropter (as determined at end of step 3);

iii) Sending this lens combination to autophoropter;

iv) Setting the angle of cylinder and axis test target 90° to angle determined in step i) and displaying on the display device;

v) Obtaining subjects responses using a keyboard or other device as to which line appears darker;

vi) Determining whether the response is the more clockwise line, if so then rotate target about 3 degrees clockwise, or if the response is the more counter clockwise line, then rotate the target about 3 degrees counter clockwise;

vii) Determining subjects response to a new position of the two lined astigmatic fan target;
   a) if response is the same as previous response then rotate target about 3 degrees more in same direction;
   b) if nor the same, rotate target one degree in opposite direction;

viii) Continuing with the above test to obtain first final angle until either;
   a) subject's response indicates no differences between darkness of lines;
   b) direction of rotating target is reversed a second time, in which case add or subtract 0.5 degree to last angle depending on last direction of rotation;

ix) Recording the first final angle on file;

x) Setting new axis for testing lens 45° from first axis (derived from step i) and repeat steps i) to ix) to obtain second final angle, and record on file;

xi) Determining subjects residual astigmatic correction using the first and second final angles obtained in steps ix) and x) and the testing lenses spheres cylinders and axes;

xii) Obtaining the corrected residual astigmatic correction by applying the least cylinder power regression equation to the residual astigmatic correction derived from step xi);

xiii) Determining the calculated sphere, cylinder, and axis by adding the residual astigmatic correction (obtained from step xi)) to initial sphere cylinder and axis, using the lens addition formula;

xiv) Determining the regression-corrected-calculated sphere, cylinder, and axis by adding the corrected residual astigmatic correction (obtained from step xi) to the initial sphere, cylinder and axis (obtained in step 3, the red-green test) using the lens addition formula and send this information is sent to the autophoropter;

xv) Displaying a line of test types on a display device;

xvi) Determining subjects preference for clarity of test types to both the initial sphere, cylinder and axis (obtained in step 3, the red-green test), and to the regression-corrected-calculated sphere, cylinder, and axis (determined in step xiv));
   a) if the initial sphere, cylinder and axis is preferred, end procedure;
   b) if the regression-corrected-calculated sphere, cylinder, and axis is preferred then continue to step xvii);

xvii) Repeating step xvi) using the regression-corrected-calculated sphere, cylinder, and axis (determined in step xiv) and the calculated cylinder and axis (determined in step xiii) and store preferred lens combination in phoropter and end procedure;

5) Determining minimum cylinder power i) A line of test type is displayed on a monitor or other display device;

ii) Determining minimum effective cylinder power by obtaining subject's preferences for clarity between about 0.25 diopter changes in cylinder power; and iii) Selecting lower cylinder power when no preference is obtained when end point reached end test;

6) Determining final sphere i) Obtaining subjects visual acuity from correct or wrong reading of test types;
   a) if correct. and type size read is larger than 20/20, reduce size of test type by one Snellen size;
   b) if wrong, increase test type by one Snellen type size and proceed to step ii);
   c) if correct and type size read is smaller than 20/20, proceed to step ii);

ii) Determining subject's preference between present (determined in step 4, xvi, or step xvii)) lens combination and a modified lens combination comprising the same lens combination with about +0.25 sphere added when sent to phoropter;
   a) if present lens combination preferred, set present lens combination in phoropter and proceed to step iii);
   b) if the modified lens combination is preferred, or if there is no preferences, set lens combination with about +0.25 diopter sphere added and repeat step i);

iii) Determining subject's preference between present (determined in step ii)) lens combination and a modified lens combination comprising the same lens combination with −0.25 sphere added when sent to phoropter;

a) if present lens combination preferred or no preference, set present lens combination in phoropter and proceed to step iv);

b) if modified lens combination is preferred, set present lens combination with about −0.25 sphere added and repeat step iii);

iv) Determining visual acuity, if it is not 20/20 then reduce type size by one Snellen unit and proceed to step v), if visual acuity is 20/20 or better, end procedure;

v) Determining subject's response to reading test type as correct or wrong;

a) if correct repeat step iv);

b) if wrong increase visual acuity by one Snellen unit and end procedure;

7) Changing autophoropter, cover eye just tested and repeat step I to end of step 6 on second eye;

8) Recording all data from both eyes on file.

15. A method for determining sphere comprising:

i) Calculating the spherical equivalent of regression corrected autorefractor result;, ii) Determining the expected unaided visual acuity using a visual acuity formula;

iii) Displaying a single letter of a size corresponding to that obtained in step ii) is presented to the subject;

iv) Determining if the response of a subject to the display of step iii) is correct or wrong;

a) If the character is correctly perceived then a repeat character is displayed one size smaller and the display step (step iv) is repeated;

b) If the subject incorrectly identifies the displayed character, then a character of one size larger is displayed;

c) If this larger character has not been previously tested then the display step (step iv) is repeated;

d) If the character has been previously displayed then proceed to next step (v);

v) Determining whether regression corrected autorefractor result (obtained from step i) is myopic, and unaided acuity is better than largest letter available, if yes then proceed to step ix), other wise, proceed to step vi);

vi) Adding an increased diopter sphere to regression corrected autorefractor spheres;

vii) Sending the sphere, obtained from step vi), along with the regression corrected autorefractor cylinder and axis to the phoropter.

viii) Testing for visual acuity as in step iv) and storing the best visual acuity;

ix) Calculating spherical equivalent using the visual acuity formula;

x) Converting the spherical equivalent to full correction using corrected autorefractor cylinder and axis (obtained from step 1);

xi) Sending the full prescription to the autophoropter.

16. A method for determining cylinder and axis comprising:

i) Determining axis at which to set testing lens from axis of cylinder present in the phoropter;

ii) Using a standard lens addition formula add testing cylinder power (about +4 diopters) and axis obtained from step i) to sphere cylinder and axis present in autophoropter (as determined at end of step 3);

iii) Sending this lens combination to autophoropter;

iv) Setting the angle of cylinder and axis test target 90° to angle determined in step i) and displaying on the display device;

v) Obtaining subjects responses using a keyboard or other device as to which line appears darker;

vi) Determining whether the response is the more clockwise line, if so then rotate target about 3 degrees clockwise, or if the response is the more counter clockwise line, then rotate the target about 3 degrees counter clockwise;

vii) Determining subjects response to a new position of the two lined astigmatic fan target;

a) if response is the same as previous response then rotate target about 3 degrees more in same direction;

b) if nor the same, rotate target one degree in opposite direction;

viii) Continuing with the above test to obtain first oval angle until either;

a) subject's response indicates no differences between darkness of lines;

b) direction of rotating target is reversed a second time, in which case add or subtract about 0.5 degree to last angle depending on last direction of rotation;

ix) Recording the first final angle on file;

x) Setting new axis for testing lens 45° from first axis (derived from step i) and repeat steps i) to ix) to obtain second final angle, and record on file;

xi) Determining subjects residual astigmatic correction using the first and second final angles obtained in steps ix) and x) and the testing lenses spheres cylinders and axes;

xii) Obtaining the corrected residual astigmatic correction by applying the least cylinder power regression equation to the residual astigmatic correction derived from step xi);

xiii) Determining the calculated sphere, cylinder, and axis by adding the residual astigmatic correction (obtained from step xi)) to initial sphere cylinder and axis, using the lens addition formula;

xiv) Determining the regression-corrected-calculated sphere, cylinder, and axis by adding the corrected residual astigmatic correction (obtained from step xi) to the initial sphere, cylinder and axis (obtained in step 3, the red-green test) using the lens addition formula and send this information is sent to the autophoropter;

xv) Displaying a line of test types on a display device;

xvi) Determining subjects preference for clarity of test types to both the initial sphere, cylinder and axis (obtained in step 3, the red-green test), and to the regression-corrected-calculated sphere, cylinder, and axis (determined in step xiv));

a) if the initial sphere, cylinder and axis is preferred, end procedure;

b) if the regression-corrected-calculated sphere, cylinder, and axis is preferred then continue to step xvii);

xvii) Repeating step xvi) using the regression-corrected-calculated sphere, cylinder, and axis (determined in step xiv) and the calculated cylinder and axis (determined in step xiii) and store preferred lens combination in phoropter and end procedure.

* * * * *